United States Patent [19]

Gambale et al.

[11] Patent Number: 4,922,923
[45] Date of Patent: May 8, 1990

[54] METHOD FOR EFFECTING A CATHETER EXCHANGE

[75] Inventors: Richard A. Gambale, Tyngsboro, Mass.; James F. Crittenden, Hollis; James P. Ryan, Amherst, both of N.H.

[73] Assignee: C. R. Bard, Inc., Murray Hill, N.J.

[21] Appl. No.: 19,626

[22] Filed: Feb. 27, 1987

Related U.S. Application Data

[62] Division of Ser. No. 766,762, Sep. 18, 1985, abandoned.

[51] Int. Cl.$^5$ .............................................. A61B 5/00
[52] U.S. Cl. .................................... 128/772; 128/657; 604/164
[58] Field of Search .................. 128/657, 772, 200.26; 604/95, 164, 166, 287

[56] References Cited

U.S. PATENT DOCUMENTS 4,545,390 10/1985 Leary ................................. 128/772

OTHER PUBLICATIONS

"Guide Wire Extension", Cope, M. D., Radiology, 1985, 157:263 published 9/24/85.

Primary Examiner—Max Hindenburg
Assistant Examiner—Randy Shay
Attorney, Agent, or Firm—Wolf, Greenfield & Sacks

[57] ABSTRACT

A guide wire system for use in catheter exchanges avoids the need for a separate exchange wire. Instead of the conventional practice in which the initial guide wire is removed and replaced with a longer exchange wire, a guide wire extension is attached to the proximal end of the initial guide wire thereby increasing its effective length so that it may be used to perform a catheter exchange. The initial guide wire remains in place in the patient's vasculature. The proximal end of the guide wire and the distal end of the exchange wire are formed to define a connection which may be crimped to effect the connection between the two wires. A crimping tool is provided to hold the mating ends of the guide wire and extension wire together while effecting the crimp.

9 Claims, 3 Drawing Sheets

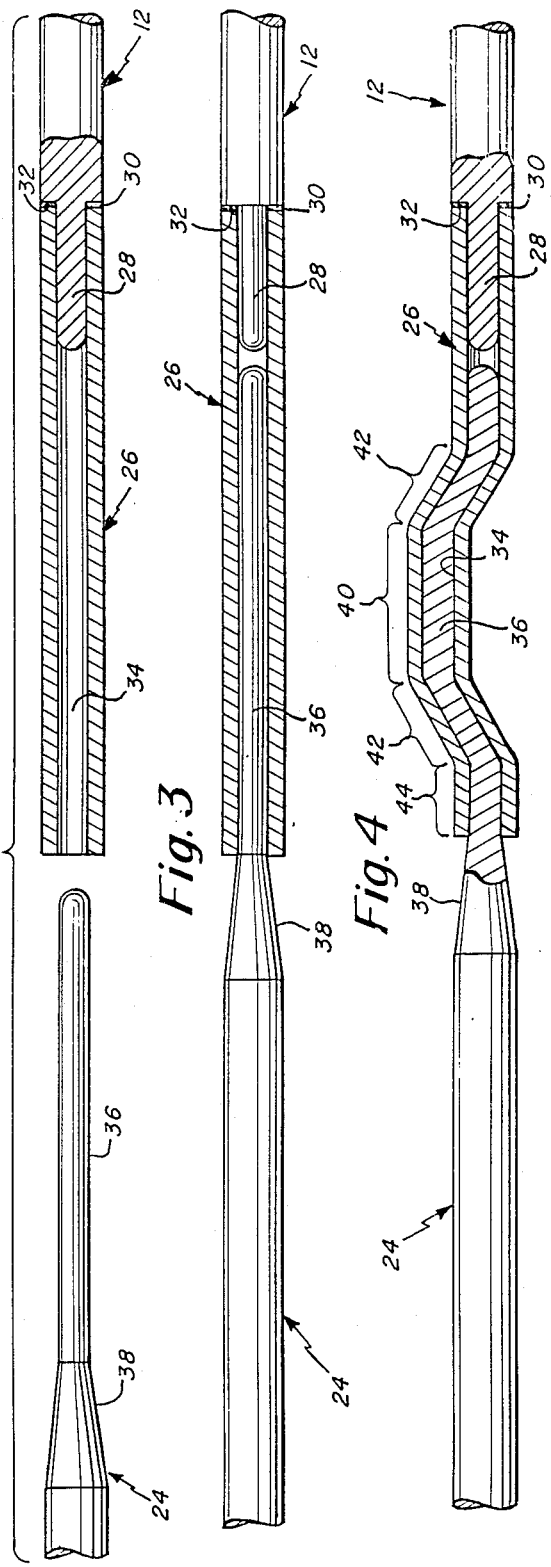

METHOD FOR EFFECTING A CATHETER EXCHANGE

RELATED APPLICATIONS

This application is a divisional of U.S. Application Ser. No. 766,762 filed Sept. 18, 1985, now abandoned.

FIELD OF THE INVENTION

This invention relates to guide wires used in vascular catheterization procedures, and to techniques for performing catheter exchanges.

BACKGROUND OF THE INVENTION

In vascular catheterization procedures it often is necessary for the physician to use different catheters in the diagnosis or treatment of a particular blood vessel. For example, when performing a coronary angiographic study, a physician commonly will use a series of catheters, to be inserted into the patient. Each of the catheters is provided with a different shape, size or configuration suited for a specific purpose. Angiographic studies typically include the use of at least three cardiac catheters including a right coronary artery catheter, left coronary artery catheter and a pigtail catheter. The three catheters each have different shapes and configurations at their distal tips. The right and left coronary artery catheters are shaped to facilitate placement of their distal outlet tips at the entries to the right and left coronary arteries, respectively. The pigtail catheter is provided with a special pigtail-shaped tip intended to reduce trauma as the catheter is advanced through the patient's tricuspid valve into the ventricle for ventricular studies. By way of further example, other types of catheters may include balloon dilatation catheters which are intended to be placed within a stenosed portion of an artery and then inflated under high pressure to expand the lumen of the artery so as to improve blood flow through the artery. In some dilatation procedures it may be desirable to use a series of dilatation catheters having different sizes or balloon configurations.

It has long been common practice in the placement of catheters to use a guide wire which is placed in the patient's artery and which is receivable in lumen of the catheter. With a guide wire in place, a catheter can be advanced over the guide wire and thereby guided to the intended vascular site. The guide wire serves to center the catheter within the blood vessel and reduces the risk of trauma to the blood vessel by the advancing catheter. The use of a guide wire reduces the risk that the distal end of the catheter might become caught on the inner surface of the blood vessel lumen. The use of a guide wire also enables the catheter to be advanced through the blood vessel relatively quickly, thereby reducing the time required for the procedure.

A standard guide wire typically is slightly longer than the catheter with which it is to be used. For example, with an angiographic catheter of the order of 130 centimeters long, the guide wire typically may be of the order of 145-175 centimeters long. When the catheter is in place over the guide wire, a relatively short portion of the guide wire protrudes proximally from the catheter. That enables the guide wire to be manipulated, if desired, from its proximal, protruding end. In that regard, it may be noted that the guide wire may be a steerable construction in which a bend is formed in its distal tip and the direction in which the bent distal tip extends it controlled by rotating the guide wire from its proximal end. For example, the guide wire may be of the type described in U.S. patent application Ser. No. 421,315 filed Sept. 22, 1982.

When it is necessary to change catheters, it usually is preferred that the catheter be removed in a manner which enables a guide wire to remain in place in the blood vessel so that the next succeeding catheter in the procedure can be inserted into the blood vessel, over the guide wire, and will be guided to the intended site in the blood vessel. In order to maintain a guide wire in place while withdrawing the catheter, the guide wire must be gripped at its proximal end to prevent it from being pulled out of the blood vessel together with the catheter. The catheter, however, is longer than the proximal portion of the guide wire which protrudes out of the patient. Thus, before the catheter is fully withdrawn it completely covers the proximally extending end of the guide wire. As a result, there is no means by which a standard guide wire can be held in place to prevent it from being withdrawn together with the catheter. If, as is often the case, it is desired to place the next succeeding catheter by advancing it over a guidewire, a new, longer guide wire is inserted in to the blood vessel and advanced into a position to provide a guide for the next catheter.

It is recognized generally as undesirable to insert, advance and withdraw a series of guide wires through a patient's blood vessels. To do so greatly increases the risk of trauma and puncture to the patient and also extends the duration of the procedure. It also requires exposure of the patient to additional radiation because of the additional fluoroscopy which would be required to place the successive guide wires In order to reduce the risk of puncture or trauma it has become a long time practice to use an exchange wire when performing catheter exchanges. The exchange wire typically is about 300 centimeters long, much longer than the typical standard guide wire. The structure of the standard and exchange wires typically is the same except for the length. The additional length of the exchange wire results in a long proximally protruding portion which is longer than the catheter to be removed. When a catheter is removed some part of the proximally extending portion of the exchange wire will always be exposed to provide a means by which the exchange wire can be gripped and its position in the blood vessel maintained. Use of the exchange wire reduces the risk of trauma to the patient because it is placed while the first catheter remains in the patient. Thus, the procedure involves initially, removal of the standard guide wire from the catheter while the catheter remains in place in the patient. Then the exchange wire is advanced through the catheter to replace the original guide wire. Because the exchange wire is guided through the patient's blood vessel by the first catheter, it does not contact the lumen of the blood vessel except, perhaps, for a small portion which protruded distally of the first catheter. The original catheter then is withdrawn over the exchange wire, which is maintained in place in the blood vessel. The next succeeding catheter then can be inserted into the patient over the exchange wire.

The foregoing system and technique of using a long exchange wire has been conventional practice for many years. The use of an exchange wire during catheter exchanges, however, is not free from difficulty. The proximally extending end of the exchange wire is quite long and cannot be manipulated easily, should it be desired to manipulate the distal end of the exchange wire. Additionally, the placement of the exchange wire must be performed under fluoroscopy to assure that it is placed properly in the patient's blood vessel. The use of an exchange wire also adds to the time and the complexity of the procedure. Notwithstanding these difficulties, the use of exchange wires has continued to be common practice in making catheter exchanges.

It is among the general objects of the invention to provide an improved guide wire system and technique by which catheter exchanges can be performed without the use of separate exchange wire and in a manner which avoids the foregoing and other difficulties

SUMMARY OF THE INVENTION

The present invention enables a catheter exchange to be made without requiring any guide wire exchanges. In accordance with the present invention a guide wire extension is attached to the proximally extending end of the guide wire while the guide wire remains in place in the patient. The guide wire extension effectively increases the length of the guide wire. After the extension is attached to the guide wire, the catheter can be withdrawn over the guide wire and its extension. The extended length enables the proximal end of the combined guide wire and extension to be exposed at all times so that its position can be maintained during removal of the catheter. Once the first catheter has been removed, the new catheter can be inserted over the combined guide wire and extension. The technique substantially shortens the duration of the procedure because the extension can be attached to the proximal end of the guide wire much faster than a conventional wire exchange can be performed. Additionally, there is a further reduction in risk of puncturing the blood vessel. There also is less exposure to fluoroscopic radiation which is required each time a guide wire is inserted.

In accordance with the invention the proximal end of the guide wire includes a connector arrangement which may be in the form of a tubular socket. The socket is receptive to a mating tip formed at the distal end of the extension wire. When the extension wire and guide wire are mated, the joint is secured, as by crimping with a special crimping tool. In the preferred embodiment, the crimp is a trapezoidal shape and is formed to have a low profile so that it will not adversely interfere with the advancement of the catheters over the crimped joint. After a successful catheter exchange, the joint can be broken to separate the extension to allow for easy manipulation of the guide wire, from its proximal end It is among the objects of the invention to provide a new and improved technique for performing catheter exchanges.

Another object of the invention is to provide a guide wire system which enables catheter exchanges to be performed without the use of an exchange wire.

Another object of the invention is to provide a technique for performing catheter exchange which is quick and requires no fluoroscopic exposure.

A further object of the invention is to provide method and apparatus for attaching an extension on to the proximal end of the guide wire while the guide wire is in place thereby to facilitate catheter exchanges over the combined guide wire extension.

Another object of the invention is to provide a system of the type described in which the extension wire can be separated from the guide wire after the catheter exchange has been completed.

DESCRIPTION OF THE DRAWING

The foregoing and other objects and advantages of the invention will be appreciated more fully from the following further description thereof, with reference to the accompanying drawings wherein:

FIG. 1 is a diagrammatic illustration of a patient undergoing catheterization with a catheter inserted percutaneously into the femoral artery and showing, diagrammatically, the catheter and guide wire which protrude proximally, and illustrating further, in phantom, the relative length of an exchange wire;

FIG. 2 is a composite fragmented and partly sectional unscaled illustration of the proximal end of a guide wire of conventional length in accordance with the present invention and the guide wire extension, showing the distal end of the extension aligned with the proximal end of the guide wire in readiness to be mated;

FIG. 3 is an unscaled illustration of the proximal and distal ends of the guide wire and extension wire of the invention when mated but before being crimped;

FIG. 4 is an unscaled illustration of the crimped connection of the guide wire an extension wire;

DESCRIPTION OF THE PREFERRED EMBODIMENT

Figure 5:
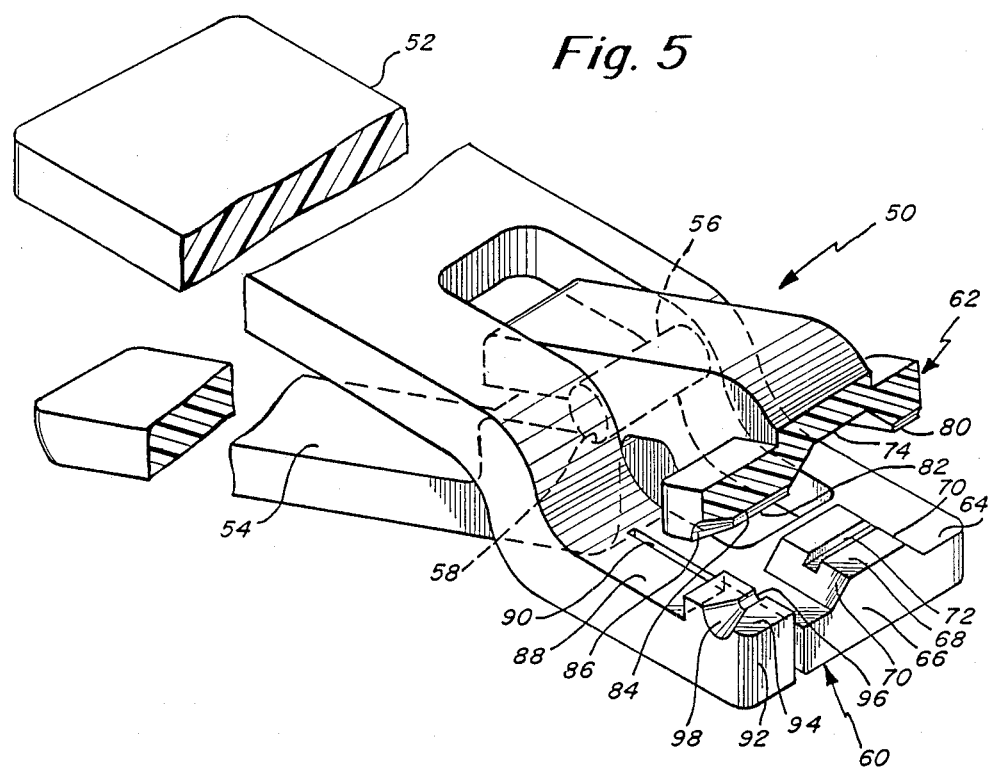
FIG. 5 is a partly fragmented and partly sectioned illustration of the crimping tool.

FIG. 1 illustrates, in highly diagrammatic form, the catheter 10 and guide wire 12 which have been inserted into the patient's femoral artery and have been advanced to the region of the patient's heart where the desired procedure will be performed. The guide wire 12 and catheter 10 will have been inserted and placed in the artery in accordance with well known procedures.

When it is desired to exchange the catheter for another, it is important that the guide wire be maintained within the patient's artery so that it may guide the next succeeding catheter quickly and efficiently to the intended site in the patient's vascular system. Typically, the clearances between the guide wire 12 and inner lumen of the catheter 10, coupled with the bends which the catheter 10 and guide wire 12 must follow along the patient's vascular system are such that withdrawal of the catheter 10 tends to drag the guide wire 12 out with the catheter 10. In order to maintain the guide wire 12 in place while the catheter 10 is withdrawn, it is necessary to hold the guide wire 12 by its proximal end 16 while withdrawing the catheter 10 over the guide wire 12. Because the proximal end 16 of a conventional guide wire only extends proximally beyond the proximal end 18 of the catheter by an amount which is substantially less than the length of the catheter 10, there is no means for retaining the conventional guide wire 12 in position while the catheter 10 is removed.

In order to effect a catheter change, it has been the practice for many years to use an exchange wire. The exchange wire is substantially longer than the conventional length of guide wire 12 and may be of the order of 300 cm long. The additional effective length of the exchange wire as compared to the conventional length guide wire 12 is represented by the phantom line 20 in FIG. 1. As illustrated in FIG. 2, the length of the exchange catheter is such that its tip, represented by the reference character 22, is spaced from the proximal end 18 of the catheter by a distance which is greater than the length of the catheter 10.

In performing the exchange, the guide wire 12 is removed from the catheter 10 while the catheter 10 remains in the patient. The exchange wire then is inserted into and advanced along the catheter 10 until its distal tip is located at the intended site within the patient's vascular system. The additional length of the exchange wire which protrudes proximally of the proximal end 18 of the catheter 10 provides a sufficiently long means by which the exchange wire may be gripped so that its position may be maintained in the patient while the catheter 10 is withdrawn. Thus, the catheter 10 may be withdrawn over the exchange wire, and the next catheter may be placed in the patient by advancing it over and along the exchange wire. After the next catheter has been placed, it may be desirable to remove the exchange wire and replace it with another standard length guide wire, depending on the type of catheterization procedure which is to be performed. For example, if the procedure requires use of a steerable guide wire which must be manipulated from its proximal end, such a guide wire will have to be exchanged for the exchange wire after the catheter exchange has been made.

In accordance with the present invention, catheters may be exchanged without requiring removal of the guide wire 12 and without requiring the involvement attendant to the use of an exchange wire. The guide wire 12 is connected, at its proximal end, to an extension wire 24 while the guide wire 12 and catheter 10 remain in the patient. The extension wire 24 is attached securely to the proximal end of the guide wire 12 and serves to extend the effective length of the guide wire 12 sufficiently to permit the catheter 10 to be withdrawn over the guide wire 12 and extension 24.

As shown in FIG. 2, the guide wire 12 is provided with a hollow tubular connective fitting 26 which is attached to and extends proximally of the proximal end of the guide wire 12. In the illustrative embodiment, the guide wire 12 is illustrated as having a proximal end formed from a solid wire such as the type of guide wire illustrated in the aforementioned U.S. patent application Ser. No. 421,315. It should be understood, however, that the general principles of the present invention may be applied to any guide wire by modifying the proximal end of the guide wire to include a means for attaching the proximal end of the guide wire to an extension wire.

In the illustrative embodiment, the proximal end of the guide wire is provided with a reduced diameter projection 28 which is received within an end of the tube which forms the connective fitting 26. The tube 26 is secured to the guide wire 12 such as by brazing as indicated at 30 at the junction of the end of the tube 26 with the shoulder 32 defined at the transition of the guide wire 12 to the reduced diameter projection 28. Alternate construction may have tapered portion to form the transition from the guide wire to the projection 28. The outer diameter of the tube 26 preferably is the sam as the outer diameter of the guide wire 12. The tube 26 thus defines an elongated socket 34 which is receptive, as will be described, to the distal end of the extension wire 24. The tube 26 may be formed from stainless steel, as may be the guide wire 12. The tube 26 may be fabricated from readily available hypodermic tubing. The wall thickness of the tube 26 should be selected so that it can be crimped easily, as will be described, but it also must be capable of providing sufficient rigidity to maintain a secure connection to the guide wire extension 24. By way of dimensional example, with a guide wire of the type described in the aforementioned U.S. patent application Ser. No. 421,315, the proximal end of the guide wire may have an outer diameter of the order of 0.016 inches and the tubing 26 will have the same outer diameter. A wall thickness for the tubing of the order of 0.0015 to about 0.003 inches has been found to be satisfactory. The length of the tubing 26 may be of the order of about four inches and the socket may be of the order of about three inches deep.

The guide wire extension 24 also may be formed from stainless steel and preferably is of comparable diameter to that of the guide wire 12 and extension 26. The distal end of the extension 24 has a reduced diameter tip 36 which is insertable into the socket 34 of the fitting 26. The guide wire extension 24 may be provided with a tapered transition region 38 between its main body and the tip 36. By way of dimensional example, in the illustrative embodiment, the tip 36 may be of the order of about four cm long having an outer diameter of 0.008–0.009 inches so that it may be received within the socket 34. The tip 36 and socket 34 should be sufficiently long so that the full length of the tip 36 extends into the socket 34.

FIG. 3 illustrates the manner in which the guide wire 12 and guide wire extension 24 mate. The distal tip of the extension simply is inserted into the socket 34 of the fitting 26. The connected members then are deformed, preferably in a configuration illustrated in FIG. 4, to secure the wire 12 and extension 24 together. Once secured, the effective length of the wire 12 will have been extended and the catheter 10 can be removed over the combined effected extended length without requiring removal of the guide wire 12.

The mechanical attachment is effected preferably by deforming the connected tube 26 and tip 36 by displacing a segment of them laterally of the common axis X of the combined guide wire 12 and extension 24 in what may be considered as a generally U-shaped configuration. The extent of lateral displacement, however, is limited by the flexibility of the catheters with which the device is to be used. The extent of lateral displacement should not be so great or sharp so as to require so sharp a bend in the catheter that it will interfere with smooth advancement of the catheter 10 over the joint. In accordance with the present invention, it has been found that a trapezoidal shaped deformation seems to provide the best results, although other non-trapezoidal shapes might be employed. As shown in FIG. 4, the preferred shape of the crimp includes a central segment 40 and a pair of spaced segments 42 which are formed between the ends of the tube 26. Preferably the crimp is formed in a manner which leaves a short proximal segment 44 of the tubing 26 which remains in coaxial alignment with the extension wire 24. In the preferred embodiment, the spaced segments 42 are arranged at an angle A of about 30° to the central axis of the guide wire 12 and extension 24. The central crimped segment 42 is displaced transversely of the axis X but extends substantially parallel to it. Preferably, the central segment 40 can be displaced about 0.060 inches from the common axis X. The overall length of the crimp including the end segments 42 and central segments is of the order of about 0.60 inches.

It has been found that such a connection can be made quickly and easily. It maintains sufficient tensile strength of the order of about one to two pounds force so as not to come apart during use, yet it does not interfere with advancement of the catheter as it is snaked over the crimped portion. Additionally, it should be noted that the connection also maintains sufficient compressive strength so that when the catheter is advanced over the guide wire and extension, the connection between the guide wire and guide wire extension will not collapse or otherwise become adversely deformed as a result of the compressive force resulting from pushing the catheter along the guide wire extension. Additionally, the connection may be broken easily and quickly should it be desired to separate the guide wire extension 24 from the guide wire 12. The guide wire 12, fitting 26 and guide wire extension 24 preferably all are coated with a thin film of low-friction material such as polytetrafluoroethylene to enhance the ease with which the catheter may slide over the guide wire and connected extension.

Although the principles of the invention may be applied to a wide range of sizes of guide wires and catheters, the configuration in the illustrative embodiment is useful particularly with smaller diameter guide wires for use with relatively small diameter flexible catheters. For example, the illustrative embodiment of the invention is particularly advantageous when used with guide wires of the order of 0.025 diameter and smaller which, in turn, may be used with catheters of the order of 6 French and smaller.

The invention also provides a device for facilitating connection and crimping of the connected guide wire 12 and extension wire 24. As shown in FIGS. 5-9, the crimping device indicated generally at 50 may be molded from a suitable plastic such as for example, Delrin (trade name for acetal). The crimping device 50 is somewhat in the form of pliers having a pair of handle members 52, 54 which are connected to each other at a pivot pin 56 and slot 58 formed integrally with the members 52, 54. The members 52, 54 thus are pivotable with respect to each other and define a pair of jaw members 60, 62 which are movable toward and away from each other. The jaws 60, 62 are arranged to hold the connective fitting 26 at the proximal end of the guide wire 12 in a position to receive the tip 36 of the extension wire 24. The jaws 60, 62 also include an arrangement for guiding the tip 56 of the extension wire 24 into the socket 34 of the fitting 26 and, when the extension wire and fitting 26 are mated, for effecting the crimp illustrated in FIG. 4.

One of the jaw members 60 has an inner face 64. The jaw 60 is molded to include a platform 66 which extends away from the jaw face 64. The platform is of trapezoidal configuration and includes an upper face 68 which is parallel to the inner face 64 of the jaw 60, and a pair of sloping side faces 70. The transversely extending groove 72 is formed transversely along the upper face 68 of the platform 66. The groove 72 is intended to receive and cooperate in holding the connective fitting 26. The opposing jaw 62 is formed with a trapezoidal shaped indentation 74 having surfaces corresponding to and paralleling those of the platform 66, including surfaces 70 and 72. The jaw member 62 also includes a pair of transversely extending members 76, 78 which have surfaces 80, 82. The surfaces 80, 82 extend parallel to the surface 64 of member 52 when the jaws 60, 62 are mated. As will be described in further detail, the fitting 26 may be positioned in the device by placing it along the channel 72 and then closing the jaw 62 to cause jaw surfaces 80 and 82 to engage the fitting 26 and hold it in place, ready to receive the tip 36 of the extension wire 24. The surface 82 of the jaw member 62 is provided with a transversely extending groove 84 which receives the end of the fitting 26 in a manner and for a purpose which will be described. The outer end of the groove 84 is formed to include an upwardly and transversely diverging funnel-shaped channel 86.

The jaw end of the handle member 52 includes an integrally formed elongate finger 88 which is separated from the main portion of the jaw member 60 by a slot 90. The finger is formed so that it may flex and bend with respect to the jaw 60 and handle 52. The outer end of the finger 88 is formed to include a platform 92 having an upper surface 94. The platform 92 includes a transversely extending groove 96 which communicates with transversely opening funnel-shaped channel 98. The platform 92 is located with respect to the transverse portion 78 of the jaw 62 so that when the jaws 60, 62 are brought together, the surfaces 82 and 94 will butt against each other with the grooves 84, 96 cooperating to define a guiding passage and the channels 86, 98 cooperating to define a funnel leading into the guiding passage.

Figure 6:
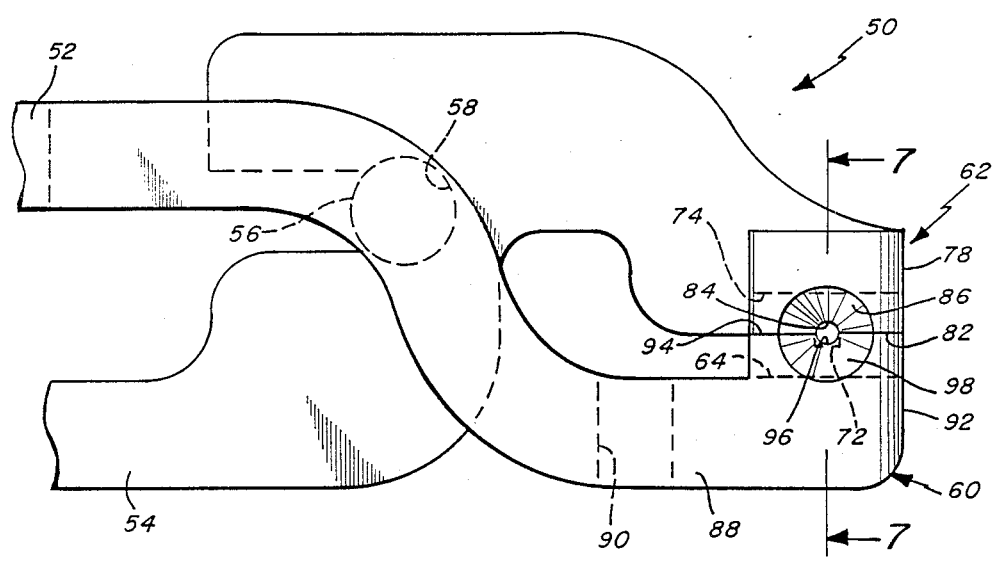
FIG. 6 is a side elevation of the jaw end of the crimping tool with the jaws closed to a wire gripping position.
Figure 7:
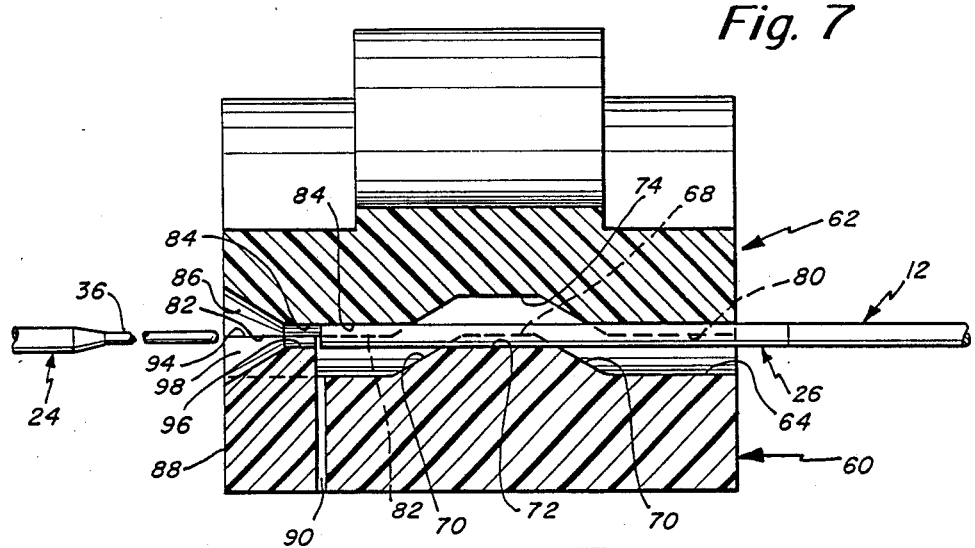
FIG. 7 is a sectional illustration as seen along the line 7—7 of FIG. 6 illustrating the jaws gripping the proximal end of the guide wire in readiness to receive the guide wire extension.
Figure 8:
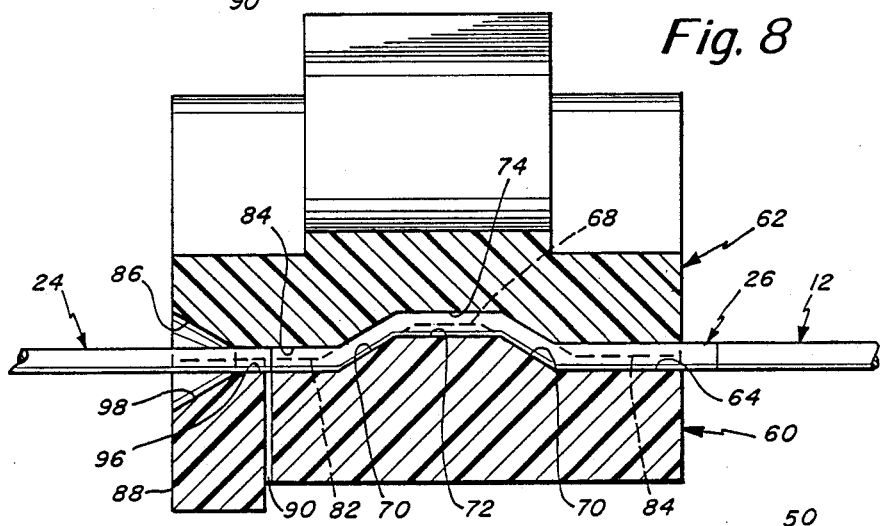
FIG. 8 is an illustration similar to FIG. 7 with the extension wire and guide wire connected and with the jaws of the crimping tool in a crimped configuration.
Figure 9:
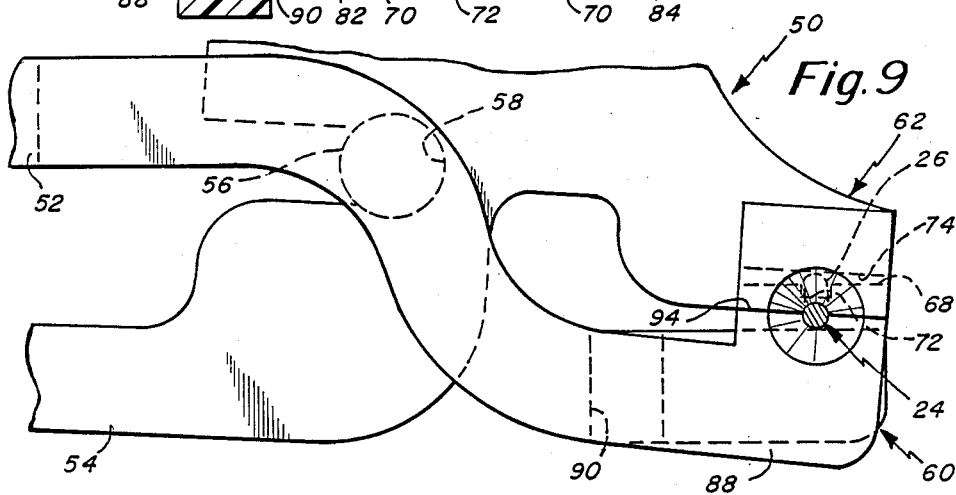
FIG. 9 is a side elevation of the jaws of the crimping tool in crimped configuration as seen along the line 9—9 of FIG. 8.

As shown in FIGS. 6 and 7 the connective fitting 26 is held between the jaws 60, 62 with the fitting 26 being engaged by the channel 72 on the platform 66 and by the surfaces 80 and groove 84 of the jaw member 62. The fitting 26 thus is held securely and its socket 34 is in alignment with the guiding passage defined by the cooperating grooves 84, 96. The distal tip 36 of the extension wire 24 then may be passed through the funnel 86 and into the aligned socket 34. The funnel defined by the channels 86, 98 serves to facilitate entry of the tip 36 into the socket 34.

Once the distal tip 36 of the extension wire has bee inserted through the funnel and guiding passage into the socket 34, the crimping tool is operated to draw the jaws 60, 62 together and effect the crimping operation. During the crimping operation, the finger 88 flexes downwardly as shown in FIG. 7 to maintain the axial alignment of the guide wire 12 and extension wire 24 which are located proximally and distally of the crimp. After the crimp has been completed, the jaws 60, 62 are opened to release the connected wires 12, 24. The guide wire 12 thus has been effectively extended so that the catheter 10 may be removed without requiring withdrawal of the guide wire 12 and insertion of a new exchange wire. After the extension has been attached and the catheter has been withdrawn, the next succeeding catheter is advanced over the extension and the guide wire into and through the patient's blood vessel. Depending on the technique involved and the physician's preference, the extension may be permitted to remain attached to the guide wire or may be separated easily. Separation can be effected by cutting the guide wire distally of the crimp.

From the foregoing, it will be appreciated that the invention provides a technique and devices by which catheter exchanges may be made in a manner which shortens the time required for the procedure, reduces the amount of radiation exposure to the patient and reduces further the risk of trauma to the patient. It should be understood, however, that the foregoing description of the invention is intended merely to be illustrative thereof and other embodiments and modifications may be apparent to those skilled in the art without departing from its spirit.

Having thus described the invention, what I desire to claim and secure by Letters Patent is:

We claim:

1. A method for effecting a catheter exchange comprising:
   providing a guide wire having a proximal end and a distal end;
   providing a first catheter having a proximal end and a distal end, the first catheter being shorter than the guide wire;
   placing the guide wire within a patient's lumen so that the proximal end of the guide wire protrudes exteriorly of the patient;
   placing the first catheter in a patient's lumen over the guide wire so that the proximal end of the catheter protrudes exteriorly of the patient and with the proximal end of the guide wire protruding proximally of the proximal end of the catheter;
   providing an extension wire having a proximal end and a distal end;
   connecting the distal end of the extension wire to the proximal end of the guide wire;
   while holding either of the guide wire or extension wire to maintain the position of the guide wire in the patient's vessel, drawing the first catheter proximally over the guide wire and extension wire to remove the first catheter from the patient's lumen;
   placing a second catheter over the proximal end of the exchange wire and advancing the second catheter over the extension wire and guide wire and into the patient's lumen,
   thereby to effect said catheter change without requiring removal of the guide wire.

2. A method as defined in claim 1 further comprising: thereafter separating the extension wire from the guide wire.

3. A method as defined in claim 1 wherein said step of connecting the extension wire to the guide wire includes the step of
   providing one of said guide wire or extension wire with a tubular socket and mating said guide wire and extension wire by inserting an end of the other of said guide wire or extension wire into said socket.

4. A method as defined in claim 3 wherein said step of connecting the extension wire to the guide wire further comprises effecting a mechanical interlock between said tubular socket and said inserted end.

5. A method as defined in claim 4 wherein said step of effecting a mechanical interlock comprises mechanically crimping said mated portion.

6. A method as defined in any of claims 1, 3, 4 or 5 wherein said lumen comprises the lumen of a blood vessel.

7. A method as defined in claim 6 wherein said blood vessel comprises an artery and in which said catheter exchange is performed during catheterization of a portion of the heart.

8. A method as defined in claim 7 wherein the guide wire is steerable.

9. A method as defined in claim 6 wherein at least one of said catheters comprises a balloon dilatation catheter.

* * * * *